US012797317B2

(12) United States Patent
Binutti et al.

(10) Patent No.: US 12,797,317 B2
(45) Date of Patent: Nov. 17, 2026

(54) ANTI-IMPERFECTION AQUEOUS MAKEUP REMOVING COMPOSITION

(71) Applicant: L'OREAL, Paris (FR)

(72) Inventors: Béatrice Binutti, Chevilly la Rue (FR); Elisa Sarrazin, Chevilly la Rue (FR); Sirine Hnana, Chevilly la Rue (FR); Maud Ribadeau Dumas, Chevilly la Rue (FR)

(73) Assignee: L'OREAL, Paris (FR)

( * ) Notice: Subject to any disclaimer, the term of this patent is extended or adjusted under 35 U.S.C. 154(b) by 274 days.

(21) Appl. No.: 18/719,513

(22) PCT Filed: Dec. 20, 2022

(86) PCT No.: PCT/EP2022/086897
§ 371 (c)(1),
(2) Date: Jun. 13, 2024

(87) PCT Pub. No.: WO2023/118075
PCT Pub. Date: Jun. 29, 2023

(65) Prior Publication Data

US 2025/0049665 A1 Feb. 13, 2025

(30) Foreign Application Priority Data

Dec. 21, 2021 (FR) .................................... 2114139

(51) Int. Cl.

| | |
|---|---|
| ***A61K 8/368*** | (2006.01) |
| ***A61K 8/04*** | (2006.01) |
| ***A61K 8/34*** | (2006.01) |
| ***A61K 8/81*** | (2006.01) |
| ***A61K 8/86*** | (2006.01) |
| ***A61Q 1/14*** | (2006.01) |
| ***A61Q 19/10*** | (2006.01) |

(52) U.S. Cl.
CPC .............. *A61K 8/368* (2013.01); *A61K 8/042* (2013.01); *A61K 8/34* (2013.01); *A61K 8/8147* (2013.01); *A61K 8/86* (2013.01); *A61Q 1/14* (2013.01); *A61Q 19/10* (2013.01)

(58) Field of Classification Search
CPC .......... A61K 8/368; A61K 8/042; A61K 8/34; A61K 8/8147; A61K 8/86; A61Q 1/14; A61Q 19/10
See application file for complete search history.

(56) References Cited

U.S. PATENT DOCUMENTS 12,115,172 B2 * 10/2024 Lin ........................ A61Q 19/10
12,527,728 B2 * 1/2026 Nordstrom ............. A61K 8/368

OTHER PUBLICATIONS

International Search Report and Written Opinion issued on Mar. 24, 2023 for corresponding PCT Application No. PCT/EP2022/086897.
Database GNPD [Online]; Mintel; Anonymous: "Shine Control Face Wash", Jan. 2021 XP055953056.
Database GNPD [Online]; Mintel; Anonymous: "Clarifying Facial Wash", May 2019 XP055953070.
Database GNPD [Online]; Mintel; Anonymous: "Mineral Micellar Water", Jul. 2021 XP055953049.
Database GNPD [Online]; Mintel; Anonymous: "Micellar Cleansing Water", Nov. 2017 XP055953236.
Database GNPD [Online]; Mintel; Anonymous: "Mild Cleansing Gel for Face and Eyes", Mar. 2015 XP055953238.
Preliminary Search Report and Written Opinion issued on Aug. 22, 2022 for corresponding French Application No. FR 2114139.

* cited by examiner

*Primary Examiner* — Timothy R Rozof
(74) *Attorney, Agent, or Firm* — POLSINELLI PC

(57) ABSTRACT

The present invention relates to a composition, preferably a cosmetic makeup removal and/or cleansing composition for keratin materials, comprising an aqueous phase comprising:
at least one compound chosen from salicylic acid and derivatives thereof,
at least one $C_2$ to $C_6$ alkanol,
at least one gelling polymer chosen from crosslinked (meth)acrylic acid homopolymers and crosslinked acrylic acid and C10-C30 alkyl acrylate copolymers, and
at least one poloxamer.
It also relates to a method for makeup removal and/or cleansing of keratin materials using such a composition.

20 Claims, No Drawings

ANTI-IMPERFECTION AQUEOUS MAKEUP REMOVING COMPOSITION

The present invention relates to a cosmetic composition, particularly a gelled micellar water, comprising an aqueous phase comprising at least one (meth)acrylic acid type gelling homo- or copolymer, anti-imperfection active agents and at least one poloxamer type surfactant.

Skin makeup removal is very important for the care of keratin materials, particularly the skin, lips, but also keratinous fibers such as the eyelashes. It must be as effective as possible because fatty residue, such as excess sebum, residue of cosmetic products used daily and makeup products, accumulate particularly in the skin folds and on the surface of the skin, and can obstruct the pores of the skin and thus cause the appearance of pimples.

In particular, makeup removal is important for subjects with combination or oily skin, or acne-prone skin.

Sebum secretion is a normal phenomenon and beneficial for both the skin and hair.

However, sebaceous hypersecretion can particularly cause pilosebaceous follicle obstruction and the formation of retention lesions or comedones, which can give rise to acne and/or hyperseborrhea.

Oily or hyperseborrheic skin is characterized by skin that is shiny, sometimes oily and thick in appearance, with dilated pilosebaceous pores.

Oily acne-prone skin therefore displays skin imperfections, dilated pores, an inhomogeneous skin texture and red blotches. The cosmetic treatment of this skin type generally involves topical application on the skin of a mixture of compounds making it possible to act upon the different causes of imperfections and particularly control sebum production.

Furthermore, more generally, oily skins, including acne-prone skins, display imperfections such as blackheads, acne marks, visible marks, visible pores and/or pimples.

These imperfections are perceived as unsightly by the subject.

Thus, it remains necessary to have compositions that combat skin imperfections effectively while respecting sensitive skins.

Moreover, most makeup removal compositions available are two-phase compositions, i.e., consisting of two separate phases, in particular an aqueous phase and an oily phase, that require prior shaking before application. Such formulations allow for good makeup removal, but leave a finish on the skin that is often oily.

There are also micellar waters, which are single-phase fluid compositions that give freshness to the application. Such compositions are not always effective on makeup removal and skin cleansing, and generally have no additional benefit, particularly on oily or acne-prone skins.

Therefore, there remains a need for effective makeup removal compositions, which are comfortable on application, and have a fluid texture, and which require no shaking before application, and which provide a benefit on application, and particularly a significant benefit in relation to skin imperfections in subjects with combination or oily skin, or acne-prone skin.

The Applicant surprisingly discovered that an aqueous composition comprising at least one compound chosen from salicylic acid and the derivatives thereof, at least one $C_2$ to $C_6$ alkanol, in association with at least one specific gelling polymer, and at least one poloxamer, requires no shaking before application, and enables effective makeup removal. It provides soothing on application. It particularly makes it possible to significantly reduce skin imperfections. In particular, it is effective in subjects with combination to oily to acne-prone skin, or in subjects with sensitive skin. Such effectiveness is even observed with low quantities of agents (i.e., salicylic acid or derivatives thereof and $C_2$ to $C_6$ alkanol). Furthermore, the composition has hypoallergenic properties in respect of keratin materials.

Thus, the present invention relates to a composition, preferably a cosmetic makeup removal and/or cleansing composition for keratin materials, comprising an aqueous phase comprising:

- at least one compound chosen from salicylic acid and derivatives thereof,
- at least one $C_2$ to $C_6$ alkanol,
- at least one gelling polymer chosen from crosslinked (meth)acrylic acid homopolymers and crosslinked acrylic acid and C10-C30 alkyl acrylate copolymers, and
- at least one poloxamer.

The composition according to the invention is single-aqueous phase, and has a gelled appearance.

The present invention also relates to a method for makeup removal and/or cleansing of keratin materials, preferably the skin and/or keratin fibers such as eyelashes, comprising the application on the keratin materials of a composition according to the invention.

"Keratin materials" means the skin, mucosa and/or skin appendages. Preferably, the keratin materials are the skin, particularly facial skin, mucosa such as the lips, and/or skin appendages such as eyelashes.

The constituents of the composition according to the invention are now described in more detail.

Aqueous Phase

The composition according to the invention comprises a physiologically acceptable aqueous phase. "Physiologically acceptable" means a medium compatible with keratin materials.

The composition according to the invention preferably comprises an aqueous phase comprising water and optionally one or several organic solvents soluble in water at 25° C. These solvents can advantageously be chosen for example from polyols particularly with 2 to 20 carbon atoms, preferably 2 to 6 carbon atoms such as glycerol, diglycerol, propyleneglycol, isoprene glycol, dipropyleneglycol, butylene glycol, hexylene glycol, 1,3-propanediol, pentylene glycol, polyethyleneglycols with 2 to 200 ethylene oxide units, and mixtures thereof.

The composition generally comprises from 50 to 99% by weight of water with respect to the total weight of the composition, preferably from 60 to 98% by weight, preferably from 80% to 95% by weight.

The quantity of organic solvent(s) can range for example from 0.01 to 15% by weight, preferably from 0.5 to 13% by weight, more preferably from 1 to 10% by weight with respect to the total weight of the composition.

The aqueous phase of the composition according to the invention also comprises at least one compound chosen from salicylic acid and derivatives thereof, at least one $C_2$ to $C_6$ alkanol, at least one gelling polymer chosen from crosslinked (meth)acrylic acid homopolymers and crosslinked acrylic acid and C10-C30 alkyl acrylate copolymers, and at least one poloxamer.

Salicylic Acid and Derivatives Thereof

The composition according to the invention comprises at least one compound chosen from salicylic acid and derivatives thereof.

Salicylic acid, or 2-hydroxybenzoic acid, is an active agent, particularly an anti-imperfection agent.

Alternatively, a salicylic acid derivative is present. The salicylic acid derivatives are preferably those of formula (I):

[Chem 1]

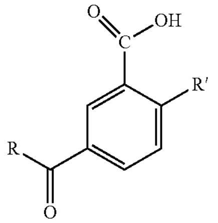

(I)

wherein:

the radical R denotes a saturated, linear, branched, or cyclic aliphatic chain having from 2 to 22 carbon atoms; an unsaturated chain having from 2 to 22 carbon atoms containing one or more double bonds capable of being conjugated; an aromatic nucleus bound to the carbonyl radical directly or by means of saturated or unsaturated aliphatic chains having from 2 to 7 carbon atoms; said nuclei and chains optionally being substituted by one or more substituents, identical or different, chosen from (a) halogen atoms (b) the trifluoromethyl group, (c) hydroxyl groups in free form or esterified by an acid having from 1 to 6 carbon atoms or (d) a carboxyl function in free form or esterified by a lower alcohol having from 1 to 6 carbon atoms;

R' is a hydroxyl group or ester group of formula —O—C(O)—R1 wherein R1 denotes a saturated or unsaturated, linear or branched aliphatic chain containing from 1 to 18 carbon atoms;

as well as the salts thereof from a mineral or organic base.

Preferably:

the radical R denotes a saturated, linear, branched, or cyclic aliphatic chain containing from 3 to 11 carbon atoms; an unsaturated chain having from 3 to 17 carbon atoms and comprising one or more optionally conjugated double bonds; said hydrocarbon chains optionally being substituted by one or more substituents, identical or different, chosen from (a) halogen atoms (b) the trifluoromethyl group, (c) hydroxyl groups in free form or esterified by an acid having from 1 to 6 carbon atoms or (d) a carboxyl function in free form or esterified by a lower alcohol having from 1 to 6 carbon atoms;

R' is a hydroxyl group or ester group of formula —O—C(O)—R1 wherein R1 denotes a radical —(CH2)n-CH3 where n is a number ranging from 0 to 14;

as well as the salts thereof obtained by salification with a mineral or organic base.

The more particularly preferred compounds are those wherein the radical R is a C3-C11 alkyl group and R' denotes hydroxyl.

Further components of particular interest are those wherein R is a chain derived from linoleic, linolenic or oleic acid. Another group of particularly preferred compounds consists of compounds wherein the radical R denotes a C3-C11 alkyl group carrying a carboxyl function in free form or esterified with a lower alcohol having from 1 to 6 carbon atoms and R' denotes hydroxyl.

Among the particularly preferred compounds of formula (I), mention can be made of n-octanoyl-5-salicylic acid (or capryloyl salicylic acid); n-decanoyl-5-salicylic acid; n-dodecanoyl-5-salicylic acid; n-heptyloxy-5-salicylic acid and the corresponding salts thereof.

By way of salicylic acid derivatives, mention can be made of 5-n-octanoylsalicylic acid (or capryloyl salicylic acid), 5-n-decanoylsalicylic acid, 5 n-dodecanoylsalicylic acid or 5-n-heptyloxysalicylic acid.

The salts of these acids are also considered according to the invention. The salts can be obtained by salifying the acid in question with an organic or mineral base. By way of mineral base, alkaline or alkaline-earth hydroxylated bases can particularly be mentioned, such as for example sodium hydroxide or potassium hydroxide and ammonia. In the case of organic bases, amine or alkanolamine type bases may particularly be involved.

The compound chosen from salicylic acid and derivatives thereof is advantageously present at a rate of 0.01% to 5% by weight of the total weight of the composition, preferably from 0.05% to 2% by weight with respect to the total weight of the composition, more particularly from 0.1% to 1% by weight.

$C_2$ to $C_6$ Alkanol

The $C_2$ to $C_6$ alkanol is a $C_2$ to $C_6$ aliphatic monoalcohol. Preferably, said aliphatic monoalcohol comprises from 2 to 4 carbon atoms.

The term "aliphatic monoalcohol" denotes any saturated, linear or branched alkane compound having a single hydroxyl (OH) group. The aliphatic monoalcohol(s) present in the compositions according to the invention can be chosen from ethanol, propanol, butanol, isopropanol, isobutanol and mixtures thereof. More specifically, ethanol will be chosen.

The $C_2$ to $C_6$ alkanol is advantageously present at a rate of 0.01% to 20% by weight of the total weight of the composition in particular from 0.1% to 10% by weight and more preferably from 0.2% to 5% by weight, preferably from 0.2% to 1% by weight with respect to the total weight of the composition.

Crosslinked (Meth)Acrylic Acid Homo- or Copolymer

The composition according to the invention comprises at least one gelling polymer chosen from crosslinked (meth) acrylic acid homopolymers and crosslinked acrylic acid and C10-C30 alkyl acrylate copolymers.

The crosslinked (meth)acrylic acid homopolymers are particularly carbomers. Mention can be made by way of such homopolymers of those marketed by GOODRICH under the trade names Carbopol 940, Carbopol 941, Carbopol 980, Carbopol 981, Carbopol ETD 2001, Carbopol ETD 2050, Carbopol 2984, Carbopol 5984 and Carbopol Ultrez 10, or by 3V under the trade names Synthalen K, Synthalen L and Synthalen MS.

The composition according to the invention can also comprise at least one crosslinked (meth)acrylic acid and C10-C30 alkyl acrylate copolymer.

In this case, the acrylic acid monomer is preferably present in quantities ranging from 60 to 95% by weight with respect to the total weight of the copolymer. The C10-C30 alkyl acrylate monomer is present preferably in quantities ranging from 1 to 50% by weight and more particularly from 4 to 40% by weight with respect to the total weight of the copolymer.

The homo- or copolymer is typically partially or entirely crosslinked by at least one conventional crosslinking agent. The crosslinking agents are in particular polyunsaturated compounds. These compounds are particularly diallylphthalates, divinylbenzene, allyl (meth)acrylate, (poly)ethyleneglycol di(meth)acrylate or bis-acrylamide methylene. The content of crosslinking agent varies from 0% to 6% by weight and preferably from 0.001 to 6% by weight with respect to the total weight of the copolymer.

Of the crosslinked acrylic acid and C10-C30 alkyl acrylate copolymers, the products sold by LUBRIZOL under the trade names PEMULEN TR1, PEMULEN TR2, CARBOPOL 1382, CARBOPOL ETD 2020, CARBOPOL ULTREZ 20, CARBOPOL ULTREZ 21 (INCI name: Acrylates/C10-30 alkyl acrylate crosspolymer), and even more preferably PEMULEN TR1, and CARBOPOL ULTREZ 21 are particularly preferred.

The concentration of crosslinked homo- or copolymer (i.e., of active substance) generally ranges from 0.05 to 2% by weight with respect to the total weight of the composition, and preferably from 0.1 h 1% by weight, and even more particularly from 0.2 to 0.9% by weight.

Poloxamer (Copolymer of Propylene Oxide and Ethylene Oxide)

The composition according to the invention also comprises at least one poloxamer, which is a copolymer of propylene oxide and ethylene oxide.

Copolymers of propylene oxide (PO) and ethylene oxide (EO), also known as EO/PO polycondensates, are copolymers consisting of polyethylene glycol and polypropylene glycol blocks.

Preferably, the EO/PO polycondensate is chosen from polyethylene glycol/polypropylene glycol/polyethylene glycol triblock polycondensates, for example those having the following chemical structure:

H—(O—CH2-CH2)*a*-(O—CH(CH3)-CH2)*b*-(O—CH2-CH2)*a*-OH, in which formula a ranges from 2 to 150, and b ranges from 1 to 100; preferably, a ranges from 10 to 130, and b ranges from 20 to 80.

By way of polycondensates, mention can particularly be made of the polyethylene glycol/polypropylene glycol/polyethylene glycol triblock polycondensates marketed under the trade names “Synperonic” by Uniqema, such as the ethylene oxide, propylene oxide and ethylene oxide condensates (13 EO/30 PO/13 EO) (MW: 2900) marketed under the trade name Synperonic PE/L 64 NAA LQ (Poloxamer 184), the ethylene oxide, propylene oxide and ethylene oxide condensates (8 EO/30 PO/8 EO) (MW: 2500) marketed under the trade name Synperonic PE/L 62 (INCI name: Poloxamer 182), the ethylene oxide, propylene oxide and ethylene oxide condensates (6 EO/67 PO/6 OE) (MW: 4400) marketed under the trade name Synperonic PE/L 121 (INCI name: Poloxamer 401), the ethylene oxide, propylene oxide and ethylene oxide condensates (46 EO/16 PO/46 OE) (MW: 5000) marketed under the trade name Synperonic PE/F38 (INCI name: Poloxamer 108), the ethylene oxide, propylene oxide and ethylene oxide condensates (128 EO/54 PO/128 OE) (MW: 14,000) marketed under the trade name Synperonic PE/F108 (INCI name: Poloxamer 338), the propylene oxide and ethylene oxide condensates (11 EO/21 PO/11 OE) (MW: 2200) marketed under the trade name Synperonic PE/L44 (INCI name: Poloxamer 124), the ethylene oxide, propylene oxide and ethylene oxide condensates (5 EO/21 PO/5 OE) (MW: 1630) marketed under the trade name Synperonic PE/L42 (INCI name: Poloxamer 122), the ethylene oxide, propylene oxide and ethylene oxide condensates (98 EO/67 PO/98 OE) (MW: 12,000) marketed under the trade name Synperonic PE/F127 (INCI name: Poloxamer 407), the ethylene oxide, propylene oxide and ethylene oxide condensates (97 EO/39 PO/97 OE) (MW: 10,800) marketed under the name Synperonic PE/F88 (INCI name: Poloxamer 238) and mixtures thereof.

Preferably, the poloxamer is ethylene oxide, propylene oxide and ethylene oxide condensate (13 EO/30 PO/13 OE) (MW: 2900), particularly that marketed under the trade name Synperonic PE/L 64 NAA LQ by Croda (INCI name: Poloxamer 184).

The concentration of poloxamer (i.e., of active substance) generally ranges from 0.05 to 2% by weight with respect to the total weight of the composition, and preferably from 0.1 à 1% by weight, and even more particularly from 0.2 to 0.9% by weight.

The composition can also comprise ingredients that are commonly used in cosmetics such as additional agents, antioxidants, preservatives, perfumes, neutralizers, additional surfactants or mixtures thereof.

Obviously, a person skilled in the art will take care to choose these optional additional compounds, and/or the quantity thereof, such that the advantageous properties of the composition according to the invention are not, or are substantially not, altered by the envisaged addition.

Among the additional agents, mention can be made of carbon powder.

According to an embodiment, the cosmetic composition according to the invention can comprise a neutralizer, such as an acid and/or a base.

According to an alternative embodiment, the composition according to the invention can comprise at least one base.

The base can be chosen from mineral bases such as for example alkaline metal hydroxides, sodium hydroxide, potassium hydroxide, ammonium hydroxides, ammonia, organic bases such as for example monoethanolamine, diethanolamine, triethanolamine, triisopropylamine, tri[(2-hydroxy) 1-propyl)]amine, N,N-dimethyl ethanolamine, 2-amino 2-methyl 1-propanol, 2-amino 2-methyl 1,3-propanediol, triethylamine, dimethylaminopropylamine and amphoteric bases (i.e., bases having both anionic and cationic functional groups) such as primary, secondary, tertiary or cyclic organic amines, amino acids. By way of example of amphoteric bases, mention can be made of glycine, lysine, arginine, taurine, histidine, alanine, valine, cysteine, trihydroxymethylaminomethane (TRISTA), triethanolamine and any one of the mixtures thereof.

According to a particular embodiment, the base of the composition is chosen from sodium hydroxide, potassium hydroxide, ammonium hydroxides, ammonia, monoethanolamine, diethanolamine, triethanolamine, tromethamine and any one of the mixtures thereof.

According to a particular embodiment, the base of the composition is chosen from among sodium hydroxide, triethanolamine, and the mixture thereof.

According to a particular embodiment, the base of the composition according to the invention is present at a mass concentration less than 0.5%, preferably less than 0.25% by mass with respect to the total mass of the composition.

According to an alternative embodiment, the composition according to the invention can comprise at least one acid.

The acid can be chosen from inorganic acids such as hydrochloric acid, sulfuric acid, nitric acid, organic acids such as acetic acid, lactic acid, glycolic acid, mandelic acid, citric acid, ascorbic acid and any one of the mixtures thereof.

The acid can be chosen from organic acids, such as benzoic acid, anisic acid, and any one of the mixtures thereof.

According to a particular embodiment, the acid of the composition according to the invention is present at a mass concentration less than 0.5%, preferably less than 0.25% by mass with respect to the total mass of the composition.

The composition according to the invention can also comprise at least one additional surfactant, other than poloxamer.

This surfactant can be anionic, non-ionic, amphoteric, zwitterionic or cationic. It can be a hydrocarbon or silicon surfactant, and can have at 25° C. an HLB balance (hydrophilic-lipophilic balance) as per GRIFFIN, preferably greater than or equal to 8.

The HLB value as per GRIFFIN is defined in J. Soc. Cosm. Chem. 1954 (volume 5), pages 249-256. Reference may be made to the document "Encyclopedia of Chemical Technology, KIRK-OTHMER", volume 22, p. 333-432, 3rd edition, 1979, WILEY, for the definition of the emulsifying properties and functions of surfactant agents, in particular p. 347-377 of this reference.

Preferably, the surfactant according to the invention is chosen from:

a) anionic surfactants such as:
   - polyoxyethylenated fatty acid salts and particularly those derived from alkaline salts, and mixtures thereof;
   - phosphoric esters and their salts such as "DEA oleth-10 phosphate" (Crodafos N 10N from CRODA) or monopotassium monocetyl phosphate (Amphisol K from Givaudan);
   - sulfosuccinates such as "Disodium PEG-5 citrate lauryl sulfosuccinate" and "Disodium ricinoleamido MEA sulfosuccinate";
   - alkylethersulfates such as sodium lauryl ether sulfate;
   - isethionates;
   - acylglutamates such as "Disodium hydrogenated tallow glutamate" (AMISOFT HS-21 R marketed by AJINOMOTO) and sodium stearoyl glutamate (AMISOFT HS-11 PF marketed by AJINOMOTO) and mixtures thereof;
   - derivatives of soybeans such as potassium soyate;
   - citrates, such as Glyceryl stearate citrate (Axol C 62 Pellets from Degussa);
   - derivatives of proline, such as Sodium palmitoyl proline (Sepicalm VG from Seppic), or the Mixture of Sodium palmitoyl sarcosinate, Magnesium palmitoyl glutamate, palmitic acid and Palmitoyl proline (Sepifeel One from Seppic);
   - lactylates, such as Sodium stearoyl lactylate (Akoline SL from Karlshamns AB);
   - sarcosinates, such as sodium palmitoyl sarcosinate (Nikkol sarcosinate PN) or the mixture of Stearoyl sarcosine and Myristoyl sarcosine 75/25 (Crodasin SM from Croda); sulfonates, such as Sodium C14-17 alkyl sec sulfonate (Hostapur SAS 60 from Clariant);
   - glycinates, such as sodium cocoyl glycinate (Amilite GCS-12 from Ajinomoto).
   - C16-C30 fatty acid salts in particular those derived from amines, such as triethanolamine stearate and/or amino-2-methyl-2-propane di-ol-1,3 stearate;

b) amphoteric or zwitterionic surfactants, such as N-acylaminoacids such as N-alkyl-aminoacetates (such as trimethylglycine), disodium cocoamphodiacetate, amine oxides such as stearamine oxide or even silicone surfactants such as dimethicone copolyol phosphates such as the one sold under the trade name PECOSIL PS 100 by PHOENIX CHEMICAL;

c) non-ionic surfactants with a HLB greater than or equal to 8 at 25° C., such as:
   - esters and ethers of sugars such as the mixture of cetylstearyl glucoside and cetyl and stearyl alcohols such as Montanov 68 from Seppic;
   - oxyethylene and/or oxypropylene ethers (that may comprise from 1 to 150 oxyethylene and/or oxypropylene groups) of glycerol;
   - oxyethylene and/or oxypropylene ethers (that may comprise from 1 to 150 oxyethylene and/or oxypropylene groups) of fatty alcohols (particularly C8-C24 and preferably C12-C18 alcohols) such as oxyethylene ether of cetearyl alcohol with 30 oxyethylene groups (CTFA name "Ceteareth-30"), oxyethylene ether of stearyl alcohol with 20 oxyethylene groups (CTFA name "Steareth-20"), and oxyethylene ether of the mixture of C12-C15 fatty alcohols containing 7 oxyethylene groups (CTFA name "C12-15 Pareth-7") marketed under the trade name NEODOL 25-7 by SHELL CHEMICALS,
   - fatty acid esters (in particular C8-C24 acid, and preferably C16-C22) and polyethylene glycol (able to comprise from 1 to 150 ethyleneglycol units) such as PEG-50 stearate and PEG-40 monostearate sold under the name MYRJ 52P by ICI UNIQUEMA,
   - fatty acid esters (particularly C8-C24 acid, and preferably C16-C22 acid) and oxyethylenated and/or oxypropylenated glycerol ethers (that may include 1 to 150 oxyethylenated and/or oxypropylenated groups), such as PEG-200 glyceryl monostearate sold particularly under the trade name Simulsol 220 TM by SEPPIC; polyethoxylated glyceryl stearate with 30 ethylene oxide groups such as the TAGAT S® product sold by GOLDSCHMIDT, polyethoxylated glyceryl oleate with 30 ethylene oxide groups such as the product TAGAT O sold by GOLDSCHMIDT, polyethoxylated glyceryl cocoate with 30 ethylene oxide groups such as the product VARIONIC LI 13 sold by SHEREX, polyethoxylated glyceryl isostearate with 30 ethylene oxide groups such as the product TAGAT L sold by GOLDSCHMIDT and polyethoxylated glyceryl laurate with 30 groups of ethylene oxide such as the product TAGAT I from GOLDSCHMIDT,
   - fatty acid esters (particularly C8-C24 acid and preferably C16-C22 acid) and oxyethylenated and/or oxypropylenated sorbitol ethers (possibly containing 1 to 150 oxyethylenated and/or oxypropylenated groups), such as polysorbate 20 sold under the name Tween 20 by CRODA, polysorbate 60 sold under the trade name Tween 60 by CRODA, d) cationic surfactants such as primary, secondary or tertiary fatty amine salts, optionally polyoxyalkylene, quaternary ammonium salts, and mixtures thereof. By way of quaternary ammonium salts, mention can particularly be made of those satisfying the following general formula:

[Chem 2]

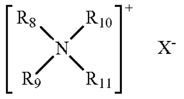

wherein:

R8 to R11, identical or different, each represent an aliphatic group, linear or branched, including from 1 to 30 carbon atoms, or an aromatic group such as aryl or alkylaryl, it being understood that at least one of the R8 to R11 groups include from 8 to 30 carbon atoms, and preferably from 12 to 24 carbon atoms. Preferably, the R8 to R11 aliphatic groups are chosen from C1-C30 alkyl groups, C1-C30 alkoxy, polyoxyalkylene (C2-C6), C1-C30 alkylamide, alkyl(C12-C22)amidoalkyl (C2-C6), alkyl(C12-C22)acetate, and C1-C30 hydroxyalkyl; and X- is an organic or inorganic anionic counter ion, such as the one chosen from halides, acetates, phosphates, nitrates, alkyl(C1-C4)sulfates, alkyl(C1-C4)- or alkyl (C1-C4)aryl-sulfonates, in particular methylsulfate and ethylsulfate.

Among the quaternary ammonium salts, preference is given to tetradecyltrimethylammonium, cetyltrimethylammonium, behenyltrimethylammonium, dipalmitoylethyl-hydroxyethylmethylammonium salts, and more particularly tetradecyltrimethylammonium bromide, behenyltrimethylammonium chloride, cetyltrimethylammonium chloride or dipalmitoylethylhydroxyethylammonium methosulfate; and e) mixtures thereof.

Preferably, the composition according to the invention comprises at least one amphoteric surfactant, such as those cited above (group b), or at least one non-ionic surfactant of HLB greater than or equal to 8 to 25° C., such as those cited above (group c), or at least one mixture of both surfactants cited above. Preferably, the composition according to the invention comprises a mixture of at least one amphoteric surfactant and at least one non-ionic surfactant chosen from fatty acid esters (particularly C8-C24, and preferably C10-C22, acid) and oxyethylenated and/or oxypropylenated sorbitol ethers (that may include from 1 to 150 oxyethylenated and/or oxypropylenated groups).

Preferably, the additional surfactant is present in the composition according to the invention in a content ranging from 0.1% to 10% by weight, preferably in a content ranging from 0.4% to 5% by weight, with respect to the total composition weight.

Such an additional surfactant indeed particularly contributes to the formation of micelles within the composition. These micelles can be detected by physicochemical methods, such as the DRX optical method.

Preferably, the composition according to the invention is substantially free from oily phase (also known as fatty phase). The term "substantially free from lipophilic phase" denotes that the composition according to the invention has an oily phase content less than or equal to 1% by weight, with respect to the total weight of the composition, preferably less than or equal to 0.5% by weight, preferably less than or equal to 0.1% by weight. Advantageously, the composition according to the invention is totally free from oily phase. Preferably, the term oil denotes a fatty substance that is in liquid form at ambient temperature (20 to 25° C.) and at atmospheric pressure (760 mm of Hg). The "fatty substance" comprises at least one "fatty" hydrocarbon chain, in other words a linear hydrocarbon chain with at least 4 carbon atoms, unsaturated or not unsaturated, possible substituted and in particular a linear C5-C30 hydrocarbon chain.

Preferably, the composition according to this invention is transparent.

The term transparent composition according to the present invention denotes a composition with a turbidity value of less than 100 NTU, preferably less than 90 NTU, preferably less than 80 NTU. Preferably, the turbidity of the compositions is equal to at least 1 NTU.

NTUs (nephelometric turbidity units) are units for measurement of the turbidity of a composition. The turbidity measurement is made, for example, with a model 2100P turbidity meter made by the Hach Company, the tubes used for the measurement being references AR397A cat 24347-06. The measurements are made at ambient temperature (from 20° C. to 25° C.).

Preferably, the composition is transparent and has a turbidity value between 1 and 100 NTU, preferably between 1 and 90 NTU, and preferably less than 80 NTU.

The present invention also relates to the use of the composition as defined hereinabove for makeup removal and/or cleansing of keratin materials, preferably the skin and/or mucosa (such as the lips) and/or keratin fibers (such as eyelashes).

The present invention also relates to a method for makeup removal and/or cleansing of keratin materials, preferably the skin and/or mucosa (such as the lips) and/or keratin fibers (such as eyelashes), comprising the application on the keratin materials of a composition according to the invention.

Throughout the application, the term "comprising a" or "including a" means "comprising at least one" or "including at least one", unless otherwise specified.

The invention is now illustrated by the following non-limiting examples. The percentages are expressed by weight with respect to the total weight of the composition (% w/w), unless specified otherwise.

EXAMPLE 1: GELLED MICELLAR WATER ACCORDING TO THE INVENTION

The aqueous composition according to the invention detailed in the table hereinafter is prepared as follows:

The ingredients of phase A are mixed, and heated at around 50° C. to 60° C. then the carbomer is added, followed by phase E.

Finally, the other ingredients are added.

TABLE 1

| Ingredient | % w/w | Phase |
|---|---|---|
| Water | 40 | A |
| BUTYLENE GLYCOL | 2 | A |
| Preservatives | QS | A |
| SALICYLIC ACID | 0.2 | A |
| CARBOMER (Carbopol 981 from Lubrizol) | 0.75 | B |
| Carbon powder | 0.0005 | C |
| Water | Qs 100 | D |
| Sodium hydroxide | 0.2125 | E |
| POLYSORBATE 20 | 0.5 | F |
| POLOXAMER 184 (Synperonic PE/L64 NAA LQ from Croda) | 0.5 | F |
| Ethanol | 0.33 | G |
| Perfume | Qs | G |
| DISODIUM COCOAMPHODIACETATE (Miranol C2M MW from Rhodia, at approximately 40% active substance) | 0.5 | H |

EXAMPLE 2: CLINICAL STUDY USING THE COMPOSITION FROM EXAMPLE 1

Purpose: Evaluation of the effectiveness of a facial cleanser (composition from example 1) on Caucasian female subjects with oily to acne-prone skin aged from 18 to 45 years, phototype I to III, after one month of twice-daily application.

Evaluation Methods and Criteria:

Counting of lesions by dermatologist: Blackheads, whiteheads, papules, pustules and erythematous macules on DO (baseline), D7 and D28;

Tolerance feedback.

Panel and Product Application:

58 Caucasian female subjects with combination to oily and acne-prone skin, aged from 18 and 45 years, phototype I to III:

Having at least 5 inflammatory lesions and 10 retention lesions on the face, excluding the nasal pyramid, vermilion border, furrow of chin and perimeter of scalp;

Having a sebumeter score 180 mg/cm$^2$.

Application:

The composition from example 1 was applied twice daily, without rinsing.

Results on Lesions on D7 (i.e., after One Week):

TABLE 2

| Lesions | Total on non-inflammatory lesions | Total on inflammatory lesions | Total on all lesions | Macules |
|---|---|---|---|---|
| Mean on D0 (baseline) | 32.81 +/− 2.45 | 22.43 +/− 1.4 | 55.24 +/− 3.12 | 5.95 +/− 0.66 |
| Mean on D7 | 18.91 +/− 1.83 | 12.09 +/− 1.02 | 31 +/− 2.44 | 4.69 +/− 0.54 |
| Significance | P < 0.001 S | P < 0.001 S | P < 0.001 S | P < 0.001 S |
| Deviation from baseline | −13.9 +/− 1.3 | −10.34 +/− 0.85 | −24.24 +/− 1.68 | −1.26 +/− 0.31 |
| % variation relative to baseline | −42% | −46% | −44% | −21% |

After one week of application of the product, all the lesions, i.e., retention and inflammatory lesions, abate on the whole face, with a statistically significant difference with respect to DO.

Results on Lesions on D28 (i.e., after Four Weeks):

TABLE 3

| Lesions | Total on non-inflammatory lesions | Total on inflammatory lesions | Total on all lesions | Macules |
|---|---|---|---|---|
| Mean on D0 (baseline) | 32.81 +/− 2.45 | 22.43 +/− 1.4 | 55.24 +/− 3.12 | 5.95 +/− 0.66 |
| Mean on D28 | 19.64 +/− 1.64 | 8.4 +/− 0.77 | 28.03 +/− 2.06 | 3.86 +/− 0.48 |
| Significance | P < 0.001 S | P < 0.001 S | P < 0.001 S | P < 0.001 S |
| Deviation from baseline | −13.17 +/− 1.43 | −14.03 +/− 1.08 | −27.21 +/− 2.07 | −2.09 +/− 0.35 |
| % variation relative to baseline | −40% | −63% | −49% | −35% |

After four weeks of application of the product, all the lesions, i.e., retention and inflammatory lesions, abate, with a statistically significant difference with respect to D0.

The invention claimed is:

1. A composition comprising an aqueous phase comprising:

at least one compound chosen from salicylic acid and salicylic acid derivatives thereof, at least one $C_2$ to $C_6$ alkanol, at least one gelling polymer chosen from crosslinked (meth)acrylic acid homopolymers, and at least one poloxamer, wherein the salicylic acid derivatives are chosen from those of formula (I):

(I)

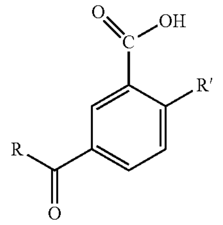

wherein:

the radical R denotes a saturated, linear, branched, or cyclic aliphatic chain having from 2 to 22 carbon atoms; an unsaturated chain having from 2 to 22 carbon atoms containing one or more double bonds capable of being conjugated; an aromatic nucleus bound to the carbonyl radical directly or by means of saturated or unsaturated aliphatic chains having from 2 to 7 carbon atoms; said nuclei and chains optionally being substituted by one or more substituents, identical or different, chosen from (a) halogen atoms (b) the trifluoromethyl group, (c) hydroxyl groups in free form or esterified by an acid having from 1 to 6 carbon atoms or (d) a carboxyl function in free form or esterified by a lower alcohol having from 1 to 6 carbon atoms;

R' is a hydroxyl group or ester group of formula —O—C(O)—R1 wherein R1 denotes a saturated or unsaturated, linear or branched aliphatic chain containing from 1 to 18 carbon atoms;

as well as the salts thereof from a mineral or organic base.

2. The composition according to claim 1, wherein the compound chosen from salicylic acid and derivatives thereof is chosen from salicylic acid, 5-n-octanoylsalicylic acid, 5-n-decanoylsalicylic acid, 5 n-dodecanoysalicylic acid and 5-n-heptyloxysalicylic acid.

3. The composition according to claim 1, wherein the compound chosen from salicylic acid and derivatives thereof is present in an amount of 0.01% to 5% by weight of the total weight of the composition.

4. The composition according to claim 1, wherein the $C_2$ to $C_6$ alkanol is an aliphatic monoalcohol comprising from 2 to 4 carbon atoms and mixtures thereof.

5. The composition according to claim 1, wherein the $C_2$ to $C_6$ alkanol is present in an amount of 0.01% to 20% by weight of the total weight of the composition.

6. The composition according to claim 1, wherein the gelling polymer is chosen from carbomers.

7. The composition according to claim 1, wherein the poloxamer is chosen from polyethylene glycol/polypropylene glycol/polyethylene glycol triblock polycondensates.

8. The composition according to claim 1, wherein the poloxamer is present in an active substance content ranging from 0.05 to 2% by weight with respect to the total weight of the composition.

9. The composition according to claim 1, comprising at least one additional agent, preferably carbon powder.

10. The composition according to claim 1, comprising at least one additional surfactant other than poloxamer.

11. The composition according to claim 1, wherein the aqueous phase comprises water and optionally at least one organic solvent soluble in water at 25° C.

12. The composition according to claim 1, characterized in that it is substantially free from oily phase.

13. The composition according to claim 1, which is transparent.

14. A cosmetic method of makeup removal and/or cleansing of keratin materials, which comprises applying to the keratin materials the composition according to claim 1.

15. A method of makeup removal and/or cleaning of the skin and/or mucosa, comprising the application on the skin and/or mucosa of a composition according to claim 1.

16. The composition according to claim 2, wherein the compound chosen from salicylic acid and derivatives thereof is present in an amount of 0.01% to 5% by weight of the total weight of the composition.

17. The composition according to claim 2, wherein the $C_2$ to $C_6$ alkanol is an aliphatic monoalcohol comprising from 2 to 4 carbon atoms and mixtures thereof.

18. The composition according to claim 3, wherein the $C_2$ to $C_6$ alkanol is an aliphatic monoalcohol comprising from 2 to 4 carbon atoms and mixtures thereof.

19. The composition according to claim 2, wherein the $C_2$ to $C_6$ alkanol is present in an amount of 0.01% to 20% by weight of the total weight of the composition.

20. The composition according to claim 3, wherein the $C_2$ to $C_6$ alkanol is present in an amount of 0.01% to 20% by weight of the total weight of the composition.

* * * * *